(12) United States Patent
Manglardi

(10) Patent No.: US 7,841,737 B2
(45) Date of Patent: Nov. 30, 2010

(54) AMBIENT LIGHTING IN SURGICAL ENVIRONMENTS

(75) Inventor: John R. Manglardi, Greenwich, CT (US)

(73) Assignee: Optimus Services LLC, Greenwich, CT (US)

( * ) Notice: Subject to any disclaimer, the term of this patent is extended or adjusted under 35 U.S.C. 154(b) by 148 days.

(21) Appl. No.: 11/996,031

(22) PCT Filed: Jul. 20, 2006

(86) PCT No.: PCT/US2006/028232
§ 371 (c)(1),
(2), (4) Date: Feb. 6, 2008

(87) PCT Pub. No.: WO2007/012043
PCT Pub. Date: Jan. 25, 2007

(65) Prior Publication Data
US 2008/0212337 A1 Sep. 4, 2008

Related U.S. Application Data

(60) Provisional application No. 60/701,106, filed on Jul. 20, 2005.

(51) Int. Cl.
*F21S 8/00* (2006.01)

(52) U.S. Cl. ............. 362/230; 362/311.01; 362/311.02; 362/311.13; 362/249.02; 362/249.16; 362/235; 362/576; 362/147

(58) Field of Classification Search ................. 362/230, 362/555, 558, 576, 147, 148, 146, 153, 235, 362/249.02, 249.16, 311.01, 311.02, 311.13
See application file for complete search history.

(56) References Cited

U.S. PATENT DOCUMENTS

| | | | | |
|---|---|---|---|---|
| 3,674,421 A | * | 7/1972 | Decupper | ................... 422/121 |
| 6,409,870 B1 | * | 6/2002 | Duffney | ..................... 156/256 |
| 7,063,449 B2 | * | 6/2006 | Ward | ......................... 362/616 |
| 7,125,137 B2 | * | 10/2006 | Kitajima et al. | ............. 362/153 |
| 2002/0143089 A1 | | 10/2002 | Minghetti et al. | |
| 2005/0099824 A1 | | 5/2005 | Dowling et al. | |

\* cited by examiner

*Primary Examiner*—Sharon E Payne
(74) *Attorney, Agent, or Firm*—Dechert LLP

(57) ABSTRACT

An ambient lighting system for a hospital operating room environment and a method of using said system is described. An apparatus comprising the combination of a translucent sheet and a backlight LED panel or colored light source (colored lamp(s) or LED(s) in an alcove) provides a diffuse light when light from said panel, alcove, or other source is presented to the translucent sheet, is scattered, and represented as unfocused light on the exposed surface of the translucent sheet. Usage of the apparatus in an operating room provides a calming environment. The method and apparatus may be adapted to include wireless control over the intensity, color, and on/off state of the light. Further, usage of known translucent materials provides a sterile and safe surface.

5 Claims, 2 Drawing Sheets

AMBIENT LIGHTING IN SURGICAL ENVIRONMENTS

CROSS REFERENCE OF APPLICATION

This application claims the priority benefit of PCT/US06/028232 filed on Jul. 20, 2006 and from provisional patent application U.S. Ser. No. 60/701,106, filed on Jul. 20, 2005 by the present inventor. The contents of PCT/US06/028232 and U.S. Ser. No. 60/701,106 are expressly incorporated herein by reference thereto.

The following references are hereby explicitly incorporated by reference thereto:

U.S. Pat. No. 6,866,410

Applications filed along with present application by current inventor on this date entitled:
- IN-CEILING FOCUS LOCATED SURGICAL LIGHTING
- HOSPITAL OPERATING ROOM RE-DESIGN
- USE OF ULTRAVIOLET GERMICIDAL IRRADIATION IN HEALTH CARE ENVIRONMENTS
- IN-WALL WASTE RECEPTACLES FOR HOSPITAL AND LABORATORY ENVIRONMENTS
- MULTIFUNCTIONAL FLOOR PODS
- RE-DESIGN OF OPERATING ROOM TABLES
- ROBOTIC FLOOR CLEANING WITH STERILE, DISPOSABLE CARTRIDGES

BACKGROUND OF THE INVENTION

1. Field of Invention

The present invention relates to devices and methods for providing ambient lighting in hospital operating room environments.

2. Background of the Invention

A typical hospital patient's experience in an operating room is a frightening experience, often worsened by the garish and harshly lighted environment. In addition to disquieting the hospital patient, sedation rates have been shown to be impacted by the nature of the room environment. As a result, an invention that improves the mood and sense of calm of a patient would be of benefit. While hospitals have begun to utilize some forms of ambient lighting in various hospital environments such as in diagnostic rooms or in routine procedure rooms such as catheterization labs, there is no adequate system for providing ambient lighting to a hospital surgical room environment. These lighting systems providing minimal lighting, i.e. an ambient light source in one small position on a wall or ceiling, and therefore do not create an immersive lighting environment. Also, the ambient lighting is provided by focusing a colored light source onto the front of a wall, typically resulting in a washed-out light. The presence of these lights in the operating room environment is conceivably a safety hazard, as they are difficult to clean (if they are cleaned at all) and provide additional surface area exposed to biohazards (thereby providing a medium for their growth). As such, a successful ambient lighting system would have to be adapted for the particular requirements of an operating room environment, namely, sterility requirements and fire, water, and electrical safety requirements.

It is an object of this invention to provide a surgical operating environment capable of supplying a diffuse ambient light, its intensity, color, and on/off state controlled wirelessly by a surgeon or other person.

It is an object of this invention to provide an immersive lighting experience.

It is a further object of this invention to provide a method of reducing anxiety in hospital patients and improving the overall sense of calm of patients and staff in hospital surgical environments by ambient lighting.

It is a yet further object of this invention to provide an apparatus and method of reducing anxiety in hospital surgical environments by ambient lighting in which the apparatus is easily sterilized and meets hospital building codes.

One or more of the above objects is met in whole or in part by this invention, and further objects may be realized by consideration of the description and claims below.

SUMMARY OF THE INVENTION

By providing a translucent sheet panel with certain properties, a back-panel containing a focused light source such as a colored LED or an alcove containing an array of bright-colored lights may be used to provide—in combination—an ambient light source. Particularly, the translucent sheet provides an ambient light source when the non-exposed surface, i.e. the surface joined with the back-panel or open to presentation from light from an alcove containing an array of bright-colored lights, is presented with a focused light source. The walls of an operating room can then be fashioned out of this translucent sheet panel allowing the room to be lit from all sides in varying intensities. Since the color of the back lighting can be changed, it produces a mood-enhancing environment that can lessen the anxiety level of a patient and provide a comfortable working environment for surgeons and staff. Further, the backlit material is preferably non-porous and of a low dielectric constant. Such a material is more sterile and is capable of being cleaned. Such backlit wall lighting is commercially available. For example, Avonite® wall covering may be used. Avonite® is a translucent material that attaches to the wall-supports much in the same way that drywall is attached. Lastly, by utilizing wireless communication devices, such as Bluetooth enabled PDAs, the LED panels or bright-colored light arrays can be controlled by integrating with them a control box containing a microprocessor adapted to control the lighting intensity, color selection, and on/off state of the LED panels.

BRIEF DESCRIPTION OF THE DRAWINGS

The present invention can best be understood in connection with the accompanying drawings. It is noted that the invention is not limited to the precise embodiments shown in drawings, in which.

BRIEF DESCRIPTION OF REFERENCE NUMERALS

100 Translucent Wall Material Slab; 102 Lit LED; 104 LED Panel; 106 LED; 108 Power Cord To/From LED To/From Control Box; 110 Control Box; 112 Power; 114 Wireless I/O; 116 Wireless Control; 118 Diffuse Ambient Light; 120 Exposed Translucent Panel Surface; 122 Non-Exposed Translucent Panel Surface; 150 Alternative Ambient Lighting System; 152 Ceiling; 154 Light Housing; 156 Light Or Light Array; 160 Wall; 162 Non-Reflected Light Beam; 164 Reflected Light Beam; 166 Ambient Light

DETAILED DESCRIPTION OF THE INVENTION

Figure 1:
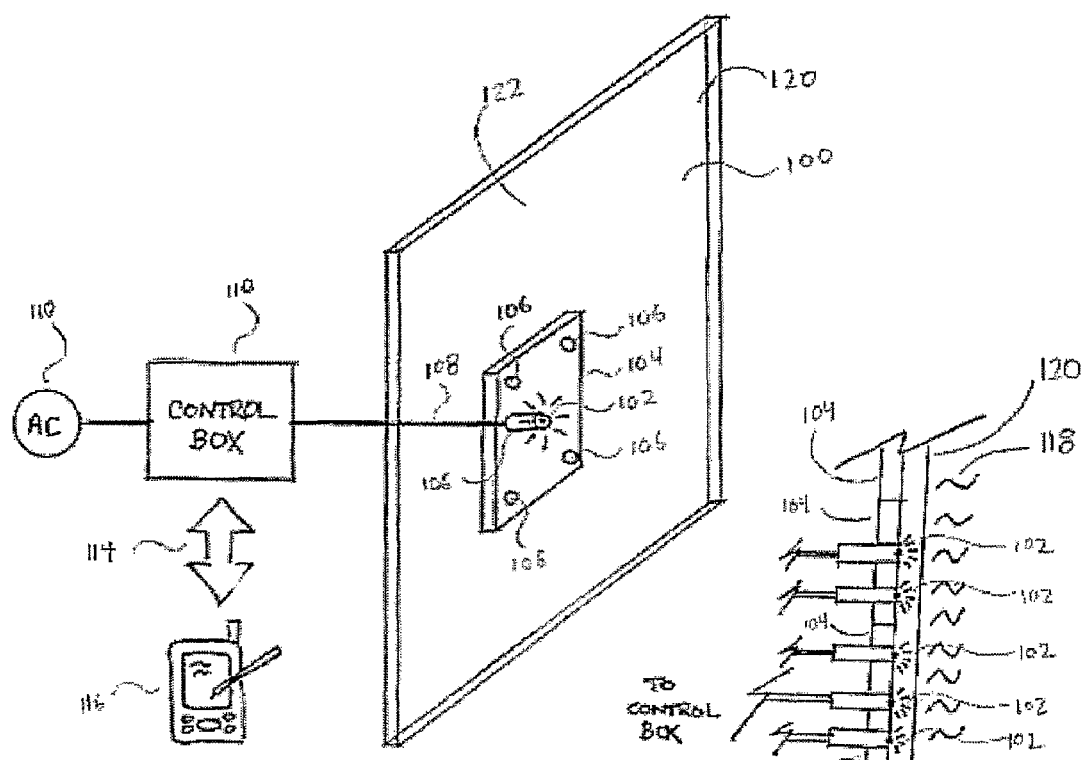
FIG. 1 is a perspective view of one embodiment with an integrated schematic overview of the wirelessly controlled ambient lighting system.
Figure 2:
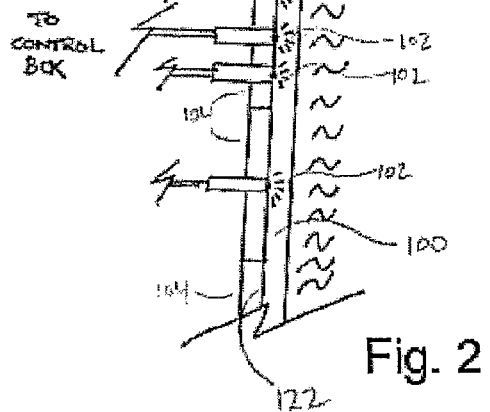
FIG. 2 is a side view of the ambient lighting system embodiment described in FIG. 1.

FIGS. 1-2 describe an embodiment of the invention.

FIG. 1 is a perspective view with an integrated schematic overview of the wirelessly controlled ambient lighting system. The surgeon utilizes a PDA or other wireless device 116 to communicate with a wireless-enabled control box 110. The control box is powered by an electrical source 112. The control box adjusts the intensity and on/off state of an LED 102. An LED capable of a single colored light or an LED capable of multiple color emissions may be used. If a single colored LED is used, multiple LEDs of various colors may be placed on the panel as shown by the four additional unlit LEDs 106. Any number of LEDs or placement of LEDs on the panels may be used as appropriate. When the LEDs are powered, focused light reaches the non-exposed—i.e. the side substantially not visible to persons in the room—surface 122 of the translucent sheet 100, which is joined with the backlight panel 104. As a result, focused light is scattered to produce a diffuse and pleasing light on the exposed surface 120.

FIG. 2 is a side view of the backlight panel 104 and translucent sheet 100 combination. Multiple lit LEDs 102 are shown producing a diffuse light 118. The backlight panels 104 are stacked next to each other and joined with the translucent sheet 100. As can be seen in the drawing, any number of LEDs may be in any one backlight panel 104. The non-exposed 122 and exposed 120 surfaces are more clearly seen in this side view drawing.

Figure 3:
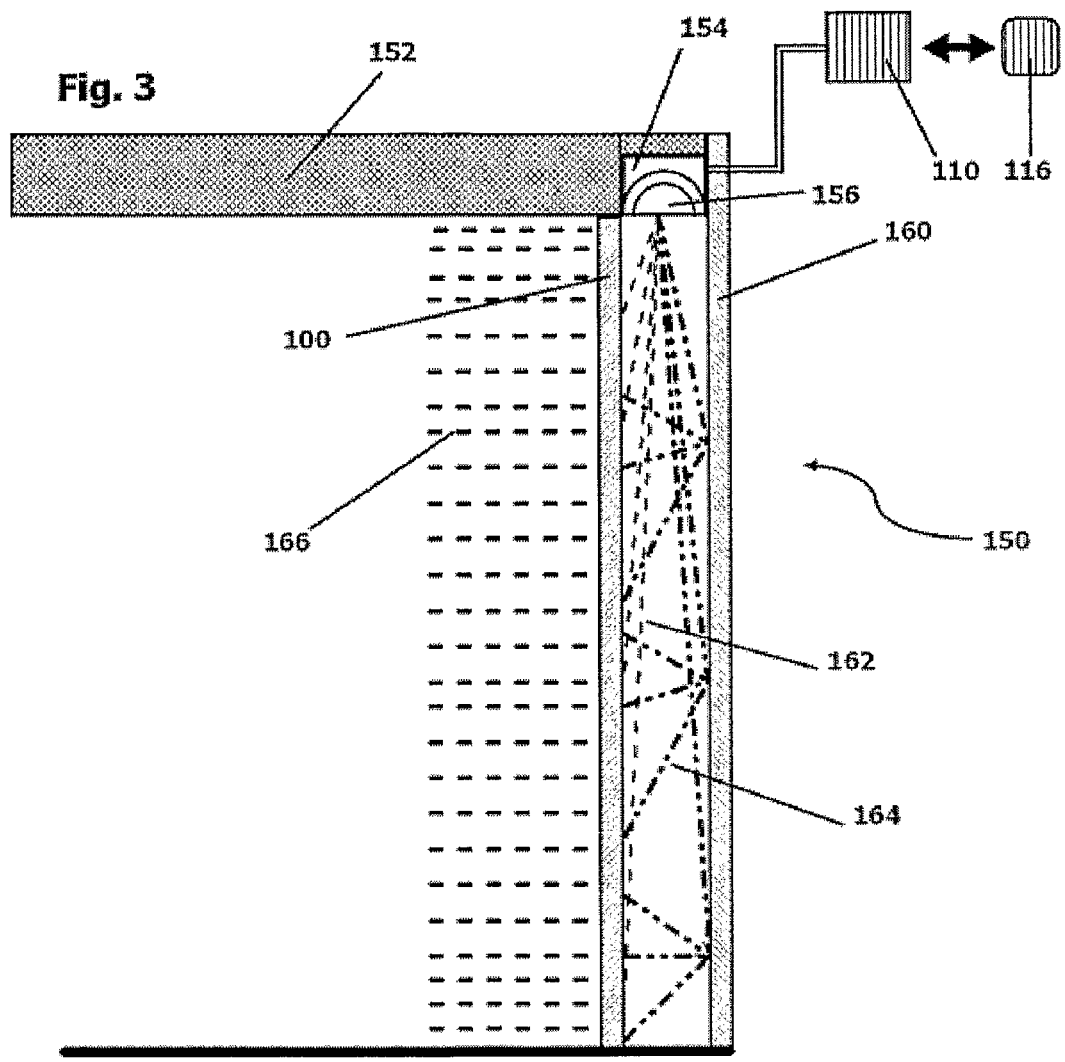
FIG. 3 is an alternative, preferred embodiment shown in side-view.
Figure 3:
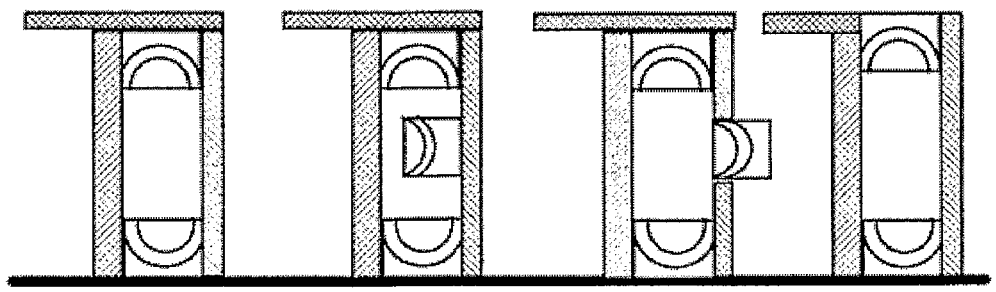

FIG. 3 shows an alternative embodiment of the invention.

FIG. 3 shows an alternative means for backlighting the translucent sheet 100 with exposed surface 120 and non-exposed surface 122. Sheet 100 may extend from the ceiling 152 to the floor. Behind sheet 100, light housing and light array 156 is placed in an alcove 154 in the ceiling 152. The alcove 154 and the light 156 may be disposed also or alternatively in the floor or in a recessed notch in wall 160. Wall 160 may optionally comprise a reflective surface, such as a mirror or polished steel. Light 156 may be an array of bright, colored halogen lights. It may also be an array of solid-state LED lighting. For example, an array of Luxeon® brand lights (from Philips®) or the Destiny CV® projection light (from TIR®) may be used. In other words, light sources that can alone or in combination with other light sources provide a bright colored light—preferably color-selectable—are acceptable.

As light from 156 reaches the non-exposed surface of 122 of panel 100, either directly (162) or by reflection (164, aided when 160 is reflective) the exposed surface 120 produces light. The surgeon can also, as in the previous embodiment, utilize a PDA or other wireless device 116 to communicate with a wireless-enabled control box 110.

In general, the translucent sheet and backlight panel or light array combination can be placed on any wall or ceiling area in an operating room. Preferably, a majority of the surfaces of the operating room are paneled with the translucent sheet. If backlight panels are used, they may be large or small and have a variable density of LEDs or other focused light sources. In one embodiment, the panels are 6 inches by 6 inches square with a depth of between 0.25 and 0.75 inches and contain 5 LEDs spaced equidistant from each other. If colored lights or colored light arrays are used, a number of dispositions of the light array are contemplated. Some of these dispositions are shown at the bottom of FIG. 3 in the four schematic representations.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention. It is further known that other modifications may be made to the present invention, without departing the scope of the invention, as noted in the appended claims.

I claim:

1. An ambient lighting system for a hospital operating room, comprising:
    at least one ambient light source, each ambient light source comprising:
        (i) a non-porous translucent sheet with a low dielectric constant, wherein the translucent sheet comprises:
            a first surface, the first surface positioned proximal to and exposed to the hospital operating room;
            an interior; and
            a second surface substantially parallel to the first surface, the second surface positioned distal to and not exposed to the hospital operating room;
        (ii) a reflector, wherein the reflector is positioned further distal to the hospital operating room than the translucent sheet and in optical juxtaposition to the translucent sheet; and
        (iii) a light source, which is optionally colored, wherein the light source is positioned so as to be capable of directly illuminating the non-exposed surface of the translucent sheet and indirectly illuminating the non-exposed surface of the translucent sheet by reflection off the reflector;
    wherein the interior and the exposed surface of the translucent sheet provide a diffuse ambient light to the hospital operating room when the lighting source directly and indirectly illuminates the non-exposed surface, and
    wherein said ambient lighting system is disposed on a majority of walls of a hospital operating room.

2. The ambient lighting system of claim 1, wherein said ambient light source is responsive to wireless control signals.

3. The ambient lighting system of claim 1 in which said translucent sheet is Avonite.

4. The ambient lighting system of claim 1 in which said light source is
    (i) a focused, colored light,
    (ii) an array of colored lights,
    (iii) an array of colored, focused lights, or
    (iv) an array of unfocused, colored lights.

5. The ambient lighting system of claim 1 in which said light source is an array of back-panels comprising at least one colored LED on at least one said back-panel.

* * * * *